United States Patent [19]

Inagaki et al.

[11] Patent Number: 4,471,786

[45] Date of Patent: Sep. 18, 1984

[54] TELEMETERING INTRACRANIAL PRESSURE TRANSDUCER

[75] Inventors: Hazime Inagaki, Nagoya; Toshikazu Ishihara, Aichi; Tomoyuki Kitano, Nagoya, all of Japan

[73] Assignee: Kabushiki Kaisha Toyota Chuo Kenkyusho, Aichi, Japan

[21] Appl. No.: 370,298

[22] Filed: Apr. 20, 1982

[30] Foreign Application Priority Data

Apr. 27, 1981 [JP] Japan ............................ 56-63606

[51] Int. Cl.³ ............................................. A61B 5/00
[52] U.S. Cl. .................................... 128/748; 128/903
[58] Field of Search ............................. 128/748, 903

[56] References Cited

U.S. PATENT DOCUMENTS

| | | | |
|---|---|---|---|
| 3,293,549 | 12/1966 | Patterson | 128/903 |
| 3,350,949 | 11/1967 | De Michele | 128/748 X |
| 3,757,770 | 9/1973 | Brayshaw et al. | 128/748 X |
| 4,246,908 | 1/1981 | Inagaki et al. | 128/748 |
| 4,354,506 | 10/1982 | Sakoguchi et al. | 128/748 |

OTHER PUBLICATIONS

Neukoum, P. A., "A Radio-Controlled Monitoring System for Multi-Channel Telemetry," Biotelemetry 1, No. 5, pp. 252-263 (1924).

Primary Examiner—Kyle L. Howell
Assistant Examiner—Francis J. Jaworski
Attorney, Agent, or Firm—Oblon, Fisher, Spivak, McClelland & Maier

[57] ABSTRACT

A telemetering intracranial pressure transducer comprises an airtight casing member housing a pressure-electric transducer for detecting an intracranial pressure, a pressure-receiving layer disposed in contact with the pressure-electric transducer and in pressed engagement with the dura under the skull, and a transmitting circuit for transmitting an output signal indicative of the intracranial pressure through a transmitting antenna. The transmitting circuit includes a telemetering transmission circuit, a microbattery and a switch for switching on and off the microbattery. The transducer thus constructed is entirely embedded below the head, dispensing with external wires or a receiving coil on the head, and detects an intracranial pressure safely and accurately without confining or disturbing the activities of a testee.

11 Claims, 7 Drawing Figures

TELEMETERING INTRACRANIAL PRESSURE TRANSDUCER

BACKGROUND OF THE INVENTION

1. Field of the Invention

The present invention relates to a telemetering intracranial pressure transducer of a small size which can be embedded below the skin of the head of a body to be tested without damaging a dura under the skull of the test body for allowing precise remote measurement of the intracranial pressure within the skull over a continued period of time.

2. Description of the Prior Art

The head of a human body to be tested is of supreme importance for the life and social life thereof. The internal pressure within the skull of the head may be varied due to external causes such as blows to the head, traffic accidents and the like, or internal causes such as intracerebral hemorrhage, encephaloma and the like. When the brain is lightly affected by such a variation in the internal pressure in the skull, the body suffers from a headache, dizziness, vomiting or the like. When the brain is severely influenced by an intracranial pressure change, there results a severe headache, consciousness loss, anaerosis or the like.

It has been practiced in the fields of cerebro-surgery and cerebro and neuro-surgery to detect the internal pressure in a skull as a method of studying causes of the foregoing symptoms and maintaining life.

One means for picking up information as to the internal pressure in the skull of a body comprises an electric pressure transducer for detecting the intracranial pressure through a hole formed in the skull. The transducer produces an electrical signal indicative of the intracranial pressure, and hence is capable of precise measurement and reliable operation. However, the electric pressure transducer needs a lead wire extending from the head of the test body to a monitoring device for indicating measurements. The patient is therefore subjected to limited activities by the lead wire. With the lead wire extending out from below the skin of the head, the lead wire has a tendency to cause the portion of the head to which the lead wire is attached to get infected with bacteria during a long period of measurement.

As a means for measuring an intracranial pressure wirelessly, there has been proposed a system in which a device with a coil or a capacitor having a variable constant is bodily embedded in the skull, and a search coil is brought from the exterior into close proximity with the coil or capacitor, whereupon the inductance of the coil or the capacitance of the capacitor is detected to measure the internal pressure in the skull. This measuring system however fails to gain a required degree of precision of measurement due to the influence of the head skin acting as a source of noises, and also fails to detect dynamic signals from within the skull.

SUMMARY OF THE INVENTION

A device according to the present invention has been successfully developed as a result of the study the inventors have made in an effort to overcome the conventional difficulties. For measuring the internal pressure in the skull of a human body, a pressure-receiving layer disposed in contact with a resilient flat portion of a semiconductor pressure-electric transducer is pressed against a dura which encloses the brain in the skull to keep the force with which the pressure-receiving layer is held against the dura and the tensioning force of the dura in equilibrium or a state of balance (a Coplanar method). The pressure upon equilibrium is picked up as an electrical signal by the semiconductor pressure-electric transducer without damaging the vital dura for simultaneous measurement of an internal pressure and a pulse pressure in the skull. The electrical signal thus obtained is transmitted wirelessly by a telemetering transmission circuit to a remote receiving circuit (e.g. at a distance of several meters).

It is accordingly an object of the present invention to provide a telemetering intracranial pressure transducer of a small size which can be embedded below the head skin of a human body and which can detect an intracranial pressure safely and accurately without confining the activities of a testee or disturbing the testee mentally with an external wire or with a receiving coil on the head of the testee.

It is another object of the present invention to provide a telemetering intracranial pressure transducer which enables an accurate detection of an intracranial pressure without the effect of the head skin of a human body.

It is a further object of the present invention to provide a telemetering intracranial pressure transducer for detecting an intracranial pressure safely without fear of infection with bacteria.

It is a still further object of the present invention to provide a telemetering intracranial pressure transducer for detecting both internal and pulse pressures in the skull stably over a wide range and for a long period of time.

A telemetering intracranial pressure transducer according to the present invention comprises: an airtight housing adapted to engage the skull of a body to be tested; a pressure-electric transducer having a pressure-sensing portion disposed in the housing for detecting an intracranial pressure below a dura under the skull; a pressure-receiving layer disposed in the housing and located at a frontal end of the housing in contact with the pressure-sensing portion of the pressure-electrical transducer, the pressure-receiving layer being in pressed engagement with the dura; and the transmitting circuit disposed in the housing. The transmitting circuit includes a telemetering transmission circuit for transmitting an output from the pressure-electric transducer, a microbattery for supplying electric power to the pressure-electric transducer and the telemetering transmission circuit, a switch for switching on and off the microbattery as desired manually or under an external magnetic field, and a transmitting antenna for transmitting out an output from the telemetering transmission circuit.

With the arrangement of the present invention, the airtight housing prevents a fluid of the test body from entering the intracranial pressure transducer. The transducer is therefore free from corrosion, and cutting of wires in the electrical circuit due to the body fluid is prevented. Other malfunctions of the transducer can be prevented which would otherwise be caused by the entry of the body fluid.

Since the intracranial pressure transducer is held in engagement with the skull of the test body, the transducer will not be displaced during measurement and hence can measure intracranial pressures for an extended period of time under equal conditions. Comparison between measured values obtained over a long span of time can be effected with ease.

With the pressure-receiving layer mounted on the frontal end of the housing, concentrated stress can be reduced which would otherwise occur upon momentary contact with the dura in the head of the testee. The pressure-receiving layer can accurately transmit a pulse pressure from the dura without attenuating such a pressure.

The pressure-electric transducer can convert an input pressure into a corresponding electrical signal with precision, so that a pressure signal corresponding to a pulse pressure transmitted from the pressure-receiving layer can be converted into an electrical signal.

Since the intracranial pressure transducer includes the telemetering transmission circuit disposed in the housing, the signal indicative of the intracranial pressure generated by the pressure-electric transducer can be electrically processed by the telemetering transmission circuit and fed out thereby from the embedded antenna by way of wireless transmission. This arrangement does not confine the person being tested to limited activities which would otherwise result from the use of lead wire. The testee is therefore free from a mental stress, and hence an intracranial pressure can be measured of the testee while in a normal mental condition.

The intracranial pressure transducer according to the present invention is embedded in a living body in most applications.

The intracranial pressure transducer of the invention may have a lead switch to be actuated under an external magnetic field or a manually actuated switch for switching on and off the power supply. The switch can be actuated as desired to reduce consumption of the microbattery as much as possible and hence increase its life time, so that the interval between replacement of such microbattery will be lengthened. The intracranial pressure transducer is thus highly practical in use.

BRIEF DESCRIPTION OF THE DRAWINGS

Various other objects, features and advantages of the present invention will be apparent from the following detailed description when considered in connection with the accompanying drawings wherein.

DESCRIPTION OF THE PREFERRED EMBODIMENTS

Figure 1:
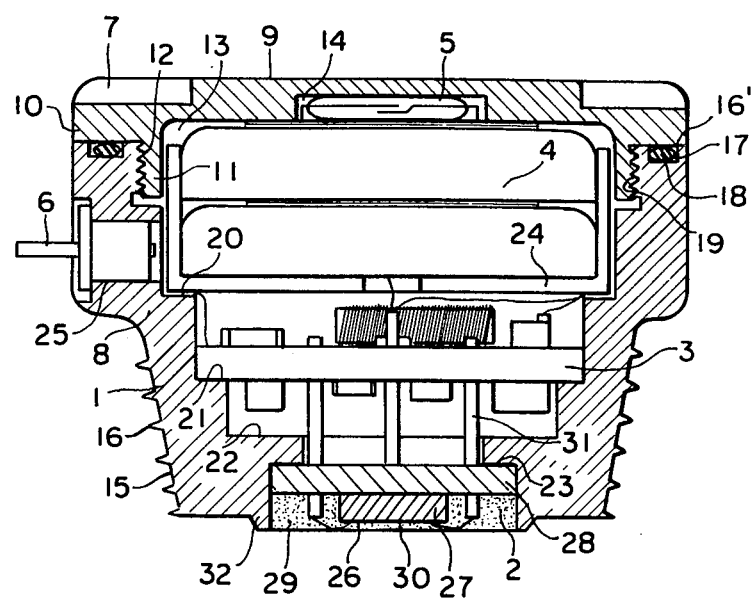
FIG. 1 is a cross-sectional view of an intracranial pressure transducer according to an embodiment of the invention.

A telemetering intracranial pressure transducer according to the present invention will be described with reference to FIGS. 1 through 4 which show an embodiment of the present invention.

The intracranial pressure transducer according to the embodiment comprises a housing 1 threadedly fixed in a hole in the skull of a human body, a pressure-electric transducer 2 mounted on a frontal end of the housing 1 for detecting an internal pressure and a pulse pressure within the skull as electrical signals, a telemetering transmission circuit 3 for modulating an output from the pressure-electric transducer 2 and transmitting out the modulated electrical signals, microbatteries 4 serving as a power supply for energizing the pressure-electric transducer 2 and the telemetering transmission circuit 3, a lead switch 5 for switching on and off the power supply or the microbattery 4 under the magnetic field generated by an external magnet, and an antenna terminal 6 for transmitting the electrical signals from the telemetering transmission circuit 3.

The housing 1 is made of stainless steel, and comprises a cover 7 and a casing 8 which coact to seal the interior of the housing in an airtight manner.

The cover 7 is in the form of a bottomed cylinder having an upper portion 9 chamfered at its periphery and a flange 10 on its lower portion which extends around an outer periphery of the cover 7 and has a predetermined width. The cover 7 also includes an annular downward projection 11 extending from an inner edge of the flange 10 thicknesswise thereof. The annular projection 11 has a threaded portion 12 around its outer peripheral surface. The cover 7 has in its bottom 13 (at an upper portion in FIG. 1) a cylindrical recess 14 which is of a diameter smaller than the inside diameter of the annular projection 11 and is concentric therewith. The lead switch 5 is mounted in the recess 14.

The casing 8 is cylindrical in shape, and has an outer peripheral surface which is tapered at 15 from an intermediate portion to a frontal end (downward in FIG. 1). The tapered surface has thereon a projected screw portion 16 for easy threaded engagement with the skull of the head to be measured of the human body.

The casing 8 has an upper flat surface 16' having therein a coaxial circular groove 17 which receives an O-ring 18 serving as an airtight seal. The upper flat surface 16' confronts a lower surface of the flange 10 of the cover 7. The casing 8 has in an upper inner wall surface adjacent to the upper flat end surface 16'a peripheral threaded groove 19 which is held in threaded engagement with a screw 12 around the outer surface of the annular projection 11 of the cover 7.

The casing 8 also has four steps 20, 21, 22, 23 therein spaced axially downwardly from the threaded groove 19 and disposed coaxially with the casing 8, the steps 20–23 being of different diameters. The step 20 has a wall of a diameter which is equal to the inside diameter of the annular projection 11 of the cover 7. A support seat 24 in the form of a bottomed cylinder is placed on an upper surface of the step 20. The microbatteries 4 (silver oxide-zinc battery) are mounted on an upper surface of the support seat 24. The step 20 has in the wall thereof a hole 25 communicating with the exterior of the casing 8. The transmission antenna terminal 6 is inserted in the hole 25. An antenna wire which is about 10 cm long is connected to the antenna terminal 6.

The step 21 has a wall of a diameter which is smaller than that of the upper step 20. A board 3 on which the telemetering transmission circuit is integrated is placed on the step 21.

The telemetering circuit board 3 is made of alumina, and the pattern of a desired circuit arrangement is printed thereon as a hybrid integrated circuit. More specifically, the circuit includes thick-film resistors, chip capacitors, and active elements such as operational amplifiers and an integrated circuit (IC). Since this arrangement allows the individual parts to be connected by printed circuit patterns which include no manual wiring connections and are highly reliable in operation. As the circuit components are concentrated in a small area, they are subjected to small temperature variations and therefore can operate stably.

The pressure-electric transducer 2 is mounted on the lowermost step 23 which is positioned at the frontal end of the housing.

The pressure-electric transducer 2 includes semiconductor strain-electric transducing elements (hereinafter referred to as "strain-sensitive elements") utilizing the piezoresistive effect of a semiconductor. The pressure-electric transducer 2 comprises a thin strain sensing member 26 of a silicon single crystal with strain-sensitive elements formed integral therewith, a first support member 27 bonded to and supporting the upper surface of the strain sensing member 26, and a second support member 28 bonded to and supporting the rear surface of the first support member 27. The pressure-electric transducer 2 is mounted in the housing 1 and a thin and resilient pressure-receiving layer 29 is disposed in contact with its surface. The layer has a predetermined contacting pressure-receiving surface and serves as a pressure transmitting portion. An airtight vacuum chamber 30 is defined on a side of the strain sensing member 26 which is opposite to the pressure transmitting portion. An external force applied to the pressure-receiving surface of the pressure-receiving layer 29 is transmitted to the strain-sensitive elements on the strain sensing member 26. The strain-sensitive elements then produce an electrical output which is fed via connectors 31 to the telemetering transmission circuit 3.

More specifically, the strain sensing member 26 which is made of a semiconductor silicon single crystal comprises pressure-electric transducing elements that have been developed by the present applicants and are extremely small and thin. The strain sensing member 26 has a thickness of 0.038 mm and is in the form of a square having a side which is 3 mm long. The strain sensing member 26 has on its central surface a pair of P-type silicon strain-sensitive elements, a signal transmitting portion contiguous to the P-type silicon strain-sensitive elements, and an electrode portion contiguous to the signal transmitting portion, these elements and portions being integrally formed on a silicon base by a diffusion process. The strain sensing member 26 has a recess in its rear surface which is opposite to the surface on which the pair of strain-sensitive elements are disposed, so that the strain-sensitive elements can detect a pressure of 0.3 atmospheric pressure.

The rear surface of the strain sensing member 26 is peripherally bonded to the first support member, while a recess which is not bonded to the first support member serves as the vacuum reference-pressure chamber 30. Thus, a strain sensing unit is formed which is centrally deformable under pressure. When such a strain sensing unit is put under a strain, the strain-sensitive elements integral with the strain sensing unit produces a variation in an electrical signal generated thereby due to the piezoresistive effect, the variation being proportional to the magnitude by which the strain sensing unit undergoes a distortion.

The first support member 27 is made of crystalized glass having a coefficient of thermal expansion which is substantially equal to that of the strain sensing member 26. The first support plate 27 bonded to the strain sensing member 26 renders the latter as less susceptible as possible to adverse influences due to changes in the ambient temperature.

The second support member 28 is made of Bakelite, and thicker and larger in outside diameter than the first support member 27. The second support member 28 is connected to the connector pins 31 for electrical connection to the pressure-electric transducer 2.

A small space is defined jointly by surfaces of the strain sensing member 26, the first and second support members 27, 28 of the pressure-electric transducer 2, and an inner periphery of an annular downward projection 32 of the casing 8. The pressure-receiving layer 29 is formed by filling the small space with a thin film of silicone resin which lies flush with the end face of the annular projection 32. The pressure-receiving layer 29 is resilient (having a modulus of elasticity of about 5 kg/cm$^2$) and has a thickness of 0.5 mm. There is thus provided a pressure transmitting chamber in which the pressure-receiving layer 29 detects a pressure imposed from the exterior and transmits such a pressure to the strain sensing member 26 of the pressure-electric transducer 2.

Figure 2:
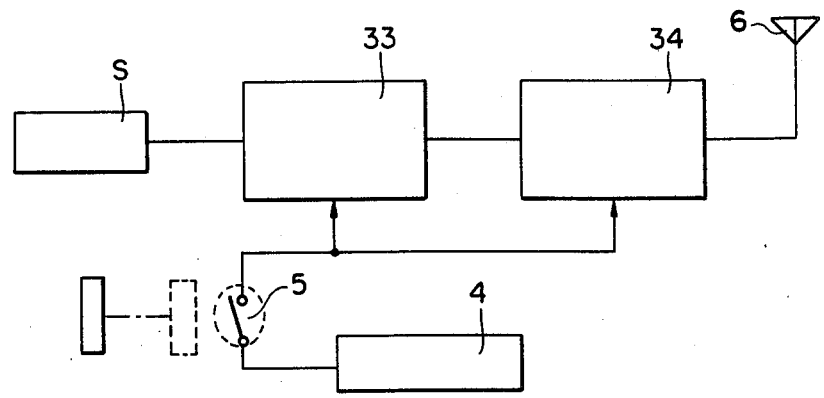
FIG. 2 is a block diagram of a transmission circuit in the intracranial pressure transducer of the invention.
Figure 3:
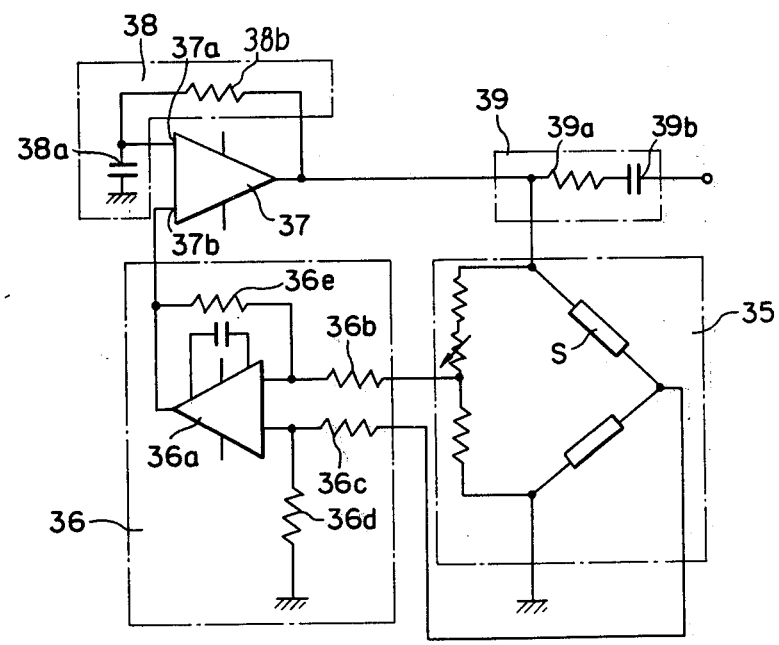
FIG. 3 is a circuit diagram of a subcarrier oscillator circuit in the transmission circuit.
Figure 4:
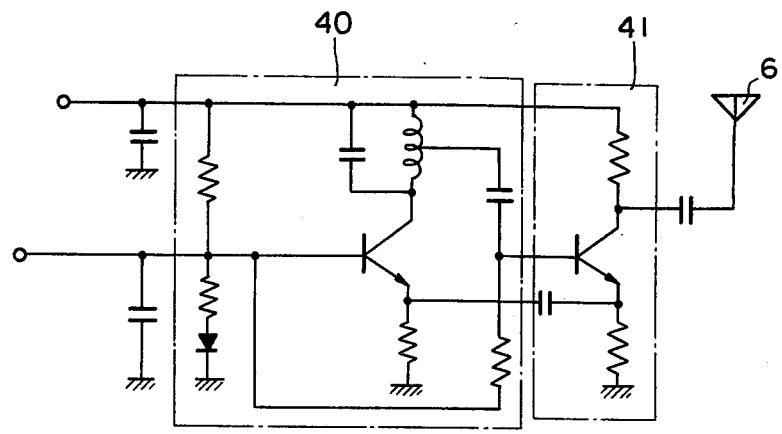
FIG. 4 is a circuit diagram of a main carrier oscillator circuit in the transmission circuit.

The electrical circuit 3 disposed in the housing 1 of the intracranial pressure transducer of the embodiment is connected as shown in FIGS. 2, 3 and 4.

The transmitting circuit comprises: a telemetering transmission circuit including a subcarrier oscillator circuit 33 connected to the pressure-electric transducer 2 for modulating an output signal therefrom into a predetermined signal and a main carrier oscillator circuit 34 for transmitting an output signal from the subcarrier oscillator circuit 33; the antenna 6 for transmitting out an output signal wirelessly; the microbattery 4 for energizing the telemetering transmission circuit 3; and the lead switch 5 for switching on and off the microbattery 4 as desired. The pressure-electric transducer 2 comprises two strain gages in a full bridge circuit 35 for converting a variation in the pressure applied into an electrical signal corresponding accurately to such a pressure variation, and for delivering the electrical signal to the subsequent subcarrier oscillator circuit 33 including the bridge circuit 35.

The subcarrier oscillator circuit 33 includes the full bridge circuit 35 having two strain gages, two resistors and a variable resistor, for detecting a change in a physical quantity to vary an oscillation frequency dependent on the detected change in the physical quantity. The subcarrier oscillator circuit 33 comprises a differential amplifier 36, the full bridge circuit 35, a comparator 37, an integrating circuit 38, and a filter circuit 39.

The differential amplifier 36 serves to amplify the difference between input signals and deliver the amplified signal as an output. The differential amplifier 36 is composed of an operational amplifier 36a, input resistors 36b, 36c, 36d, and a fixed resistor 36e for amplifying an electrical signal corresponding to the difference between input signals and for supplying the amplified signal to the comparator 37.

The comparator 37 compares two inputs, and has one input terminal 37b supplied with an output from the differential amplifier 36 and the other input terminal 37a connected to the integrating circuit 38, which comprises a capacitor 38a and a resistor 38b. The comparator 37 has an output terminal connected to the bridge circuit 35 and the filter circuit 39.

The filter circuit 39 cuts off a d.c. component in an input signal fed thereto and supplies its output to the main carrier oscillator circuit 34. The filter circuit 39 has a resistor 39a and a capacitor 39b.

The subcarrier oscillator circuit 33 of the above construction constitutes an astable multivibrator for frequency-modulating a carrier frequency (which is 24 KHz according to this embodiment) with a signal corresponding to a pressure imposed on the bridge circuit 35.

The main carrier oscillator circuit 34 operates on the principle of an LC back coupling oscillator, and comprises a Hartley oscillator 40 for modulating an oscillation frequency with the subcarrier signal from the previous stage, and a high-frequency current amplifying circuit 41 for radiating a high-frequency electric power through the antenna 6.

Since the antenna 6 is embedded in the head of the test body, it would cause difficulty if it has a prescribed length ($\lambda/4$, for example). To avoid the problem, the antenna 6 is connected electrically to the living body by an antenna wire which is about 10 cm long to utilize the body as an antenna load.

Figure 5:
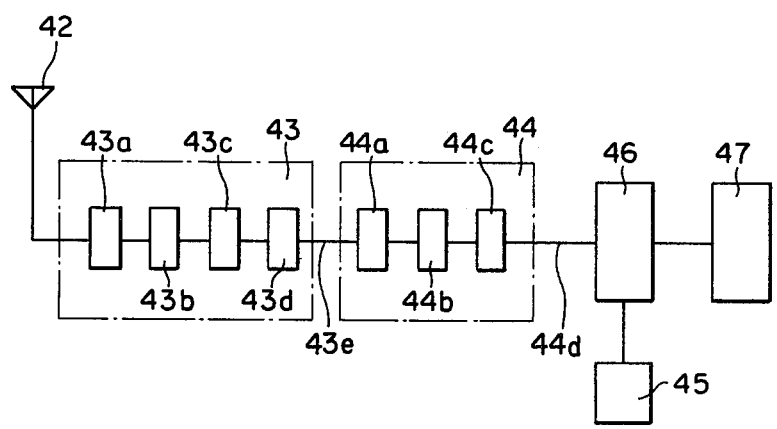
FIG. 5 is a block diagram of a receiver circuit.

A receiver has a circuit arrangement as shown in FIG. 5. The receiver comprises an antenna 42 for receiving a transmitted signal, circuit 43 for detecting a received signal, a circuit 44 for discriminating a subcarrier signal from the received signal, a correction circuit 46 for correcting the signal with a signal from a barometer 45, and an indicator 47 for indicating the corrected signal. The transmitted signal is thus indicated on the indicator 47.

The detecting circuit 43 serves to convert the high-frequency signal composed of the main carrier signal into an intermediate-frequency signal by way of a superheterodyne system, and to demodulate the subcarrier signal through FM detection. The detecting circuit 43 comprises a high-frequency amplifier 43a, a mixer 43b, an intermediate-frequency 43c, and an FM detector circuit 43d. The detecting circuit 43 has an output terminal 43e connected to the subcarrier discriminator circuit 44 at the next stage.

The subcarrier discriminator circuit 44 serves to pick up a signal corresponding to a variation in a physical quantity from the subcarrier signal in the input signal. The subcarrier discriminator circuit 44 comprises a Schmitt circuit 44a, a phase detector circuit 44b, and a filter circuit 44c for discriminating the amplitude of the input signal to effect phase-synchronized detection to gain a demodulated signal. The subcarrier discriminator circuit 44 is effective to pick up a signal reliably out of noises.

The subcarrier discriminator circuit 44 has an output terminal 44 d connected to the correction circuit 46 which comprises a differential amplifier. One of the inputs of the differential amplifier in the correction circuit 46 is supplied with a signal from the barometer 45. Thus, the correction circuit 46 produces an output indicative of the difference between an output from the receiver and an output from the barometer 45, and delivers such an output to the subsequent indicator 47. A signal indicating an atmospheric pressure applied to the intracranial pressure transducer is therefore compensated for by the barometer 45.

Figure 6:
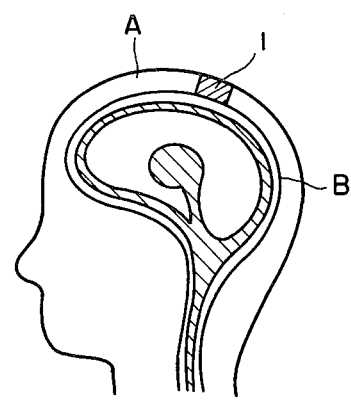
FIG. 6 is a view showing the manner in which the intracranial pressure transducer of the embodiment is used.

Operation and advantages of the intracranial pressure transducer according to the foregoing embodiment will be described with reference to FIG. 6.

Before the intracranial pressure transducer is installed for detecting an internal pressure and a pulse pressure in the skull of a person to be tested, a hole is formed in the skull A at an area in which the head is to be measured, with care being taken to bring the central axis of the hole into alignment with the central point of the head as much as possible.

The intracranial pressure transducer 1 is then threaded into the hole until the pressure-receiving layer 29 that faces the dura B below the skull A contacts the dura B. An antenna connected to the antenna terminal 6 is embedded below the skin of the head, and then the head skin is sewn up.

When a magnet is brought into close proximity with the intracranial pressure transducer embedded below the head skin, the lead switch 5 in the transducer is actuated under the magnetic field produced by the magnet, whereupon the electrical circuits are energized.

More specifically, the internal pressure and the pulse pressure in the skull A are transmitted accurately via the dura B below the skull to the pressure-receiving layer 29 mounted on the frontal end of the transducer. The transmitted internal and pulse pressures are transmitted to the strain-sensitive elements on the strain sensing member 26 of the pressure-electric transducer 2, and are converted thereby into an electric signal. The electric signal is supplied to the subcarrier oscillator circuit 33 in which the signal is frequency-modulated, and then is further modulated by the main carrier oscillator circuit 34. The modulated signal is radiated via the antenna 6 as a high-frequency electric power or radio wave.

The radio wave as radiated by the antenna 6 is received by the antenna 42 of the receiver, in which the received signal is supplied to the detecting circuit 43. The detecting circuit 43 serves to amplify the radio wave (main carrier) radiated from the telemetering intracranial pressure transducer and detect the same to reproduce the subcarrier signal. The subcarrier signal is fed to the next subcarrier discriminator circuit 44, in which a sensor signal is picked up from the subcarrier signal. The reproduced pressure signal is delivered to the correction circuit 46, in which an atmospheric pressure signal from the barometer 45 is subtracted from the pressure signal transmitted from the telemetering intracranial pressure transducer to effect atmospheric pressure compensation. The corrected signal is supplied to the indicator 47 for recording the internal pressure in the skull.

Since the frontal end 32 of the pressure-electric transducer 2 projects slightly, the frontal end 32 depresses the dura B below the skull A by the distance which the frontal end 32 projects downwardly. The projecting end 32 serves to keep the tensioning force of the dura B and the force with which the end 32 is held against the dura B in equilibrium or a state of balance, and hence acts as a correction means for accurately measuring intracranial pressures in a wide range, from a low pressure to an abnormally high pressure.

The strain sensing member 26 of the pressure-electric transducer 2 has the integral strain-sensitive elements for converting a pressure into a corresponding electric signal, an arrangement which is extremely thin and small. The strain-sensitive elements are of high sensitivity such that they can convert small pressure variations into corresponding electric signals with accuracy.

The pressure-electric transducer 2 composed of the strain sensing member 26 and the first and second support members 27, 28 which support the member 26, is mounted in the casing 8, and overlies the pressure transmitting portion which is composed of the pressure-receiving layer 29 having a predetermined pressure-receiving surface, which is thin, flexible, and has a predetermined flexibility. When a pressure is applied from the exterior to the pressure-receiving layer 29, the pressure is transmitted as an internal pressure to the pressure transmitting portion. The pressure transmitting portion is surrounded peripherally by the annular projection 32 of the casing 8, the first and second support members 27, 28 of the pressure-electric transducer 2, and the dura B under the skull A. Thus, the pressure transmitting portion is subjected to a minimum degree of free expansion. The internal pressure transmitted to the pressure transmitting portion can therefore be imposed on the strain sensing member 26 with the strain-sensitive elements thereon without being lessened or attenuated, resulting in an increased accuracy of measurement.

When the skull is bored at an area in which measurements are to be made, the dura B has a convex surface projecting radially outwardly under the internal pressure within the skull. Without the pressure-receiving layer 29, the dura would be pressed at a point against the pressure-receiving surface of the inserted intracranial pressure transducer to apply concentrated stresses directly to the strain-sensitive elements, whereupon the latter would produce abnormally high output voltages. With the pressure-receiving layer 29 being used, concentrated stresses on the pressure-sensitive elements are reduced upon contact with the dura B since the layer 29 has a predetermined thickness and resiliency.

The strain-sensitive elements disposed on the strain sensing member 26 for converting a pressure into a corresponding electric signal are highly sensitive to temperatures, and hence are subjected to drifts due to abrupt temperature changes when transferred from a storage area at a room temperature to a living body which has a temperature of about 37° C. The pressure-receiving layer 29, however, prevents such a temperature change from being conducted directly to the strain-sensitive elements, but temporarily slows down the temperature rise.

Since the pressure-receiving layer 29 is made of silicone resin, it gives the testee no physical discomfort, and hence serves to keep the testee under a stable mental condition without irritating him or her.

The lead switch 5 is actuatable manually (e.g. by pushing) or by proximity with a magnet brought near the head skin after the transducer has been embedded in the skull. The lead switch 5 serves to increase the life time of the microbattery 4 in the transducer which will be placed in the head for a long time.

Figure 7:
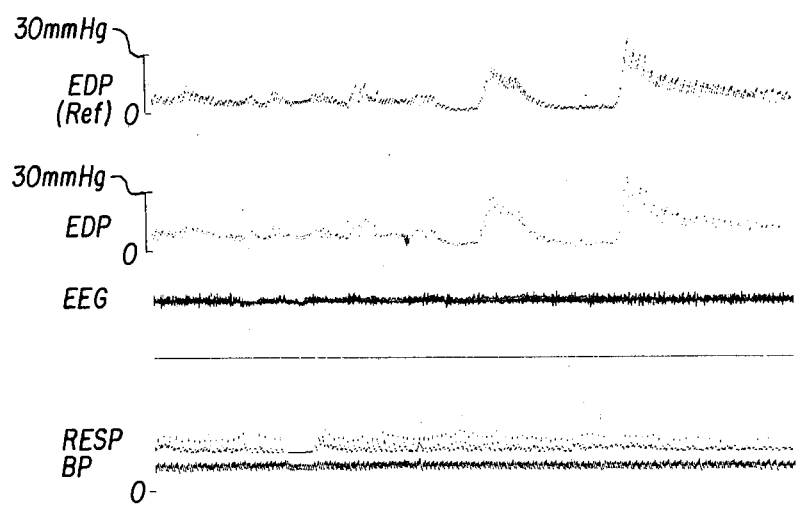
FIG. 7 is a diagram showing a wave shape of an internal pressure in the skull of a human body detected by a conventional intracranial pressure transducer and wave shapes of internal and pulse pressures detected by the transducer of the invention.

FIG. 7 shows an example in which the intracranial pressure transducer of FIG. 1 was used to detect variations in the internal and pulse pressures in a skull.

The horizontal axis of FIG. 7 indicates time that elapsed, and the vertical axis thereof is indicative of a waveform of an internal pressure within a skull (EDP as a reference) measured by a conventional intracranial pressure transducer with wire transmission, and a waveform of an internal pressure (EDP) and an electroencephalogram (EEG) measured with a wireless intracranial pressure transducer according to the embodiment of the invention, all being recorded by a pen recorder to indicate changes thereof.

As is apparent from the clinical example, the intracranial pressure transducer of the present invention can detect the internal pressure in the skull in the same manner as that in which the internal pressure is detected by a wired intracranial pressure transducer, and does not confine the test body to limited activities which would otherwise result from the use of a transmission wire. The intracranial pressure transducer of the present invention thus allows observation of intracranial pressures for a continued period of time.

With the arrangement of the invention, the pressure-receiving layer of the intracranial pressure transducer is pressed against the dura which is a living membrane below the skull of a person to be tested, until the force with which the pressure-receiving layer is held against the dura and the tensioning force of the dura are kept in equilibrium, whereupon the internal pressure in the skull is measured. The intracranial pressure transducer can measure internal and pulse pressures in the skull without damaging the dura which is a vital living membrane. With the transducer embedded in the skull of the human body to be tested, there is no danger for the body to be infected with bacteria. Therefore, the transducer of the invention is quite safe in operation. The pulse pressure in the skull can be transmitted as an electric singal wirelessly by the telemetering transmission circuit, an arrangement which allows a testee under clinical treatment to be measured for a pulse pressure within the skull over a long period of time as well as a short interval of time. Therefore, the intracranial pressure transducer of the invention is highly effective in use in the fields of cerebro-surgery and cerebro and neuro-surgery.

Obviously, numerous modifications and variations of the present invention are possible in light of the above teachings. It is therefore to be understood that within the scope of the appended claims, the invention may be practiced otherwise than as specifically described herein.

What is claimed is:

1. A telemetering intracranial pressure transducer comprising:

an airtight housing adapted to engage the skull of a body to be tested;

a pressure-electric transducer having a pressure-sensing portion, disposed in said housing for detecting an intracranial pressure below a dura under the skill wherein said pressure-electric transducer comprises two strain-sensitive elements in a full bridge circuit;

a pressure-receiving layer disposed in said housing and located at a frontal end of said housing in contact with said pressure-sensing portion of said pressure-electric transducer, said pressure-receiving layer being in pressed engagement with said dura; and a transmitting circuit disposed in said housing for transmitting an output signal from said pressure-electric transducer through a transmitting antenna wherein said transmitting circuit comprises a telemetering transmission circuit connected to said pressure-electric transducer for transmitting an output therefrom and microbatteries for supplying electric power to said pressure-electric transducer and said telemetering transmission circuit with said transmission circuit further comprising a switching means connected to said microbatteries for switching on and off said microbatteries and wherein said telemetering transmission circuit includes a subcarrier oscillator circuit connected to said pressure-electric transducer for modulating an output signal therefrom into a predetermined signal and wherein said telemetering transmission circuit further includes a main carrier oscillator circuit connected to said subcarrier oscillator circuit for transmitting an output signal therefrom with said subcarrier oscillator circuit comprising an astable multivibrator for frequency-modulating a carrier frequency including a full bridge circuit for delivering an electrical signal corresponding to a pressure variation, a differential amplifier connected to said full bridge circuit for amplifying said electrical signal therefrom, a comparator having a first input terminal, a second input terminal connected to said differential amplifier and an output terminal connected to said full bridge circuit, an integrating circuit connected to said first input of said comparator, and a filter circuit connected to said output terminal of said comparator for cutting off a d.c. component in an signal fed thereto and supplying a subcarrier signal to said main carrier oscillator circuit.

2. A telemetering intracranial pressure transducer according to claim 1, wherein
said switching means is a lead switch actuated under an external magnetic field.

3. A telemetering intracranial pressure transducer according to claim 1, wherein
said switching means is a manually actuated switch.

4. A telemetering intracranial pressure transducer according to claim 1, wherein
said pressure-electric transducer comprises
a thin strain-sensing member of a silicon single crystal having the pressure-sensing portion with strain-sensitive elements integrally formed thereon,
a first support member bonded to and supporting the upper surface of said strain-sensing member,
a second support member bonded to and supporting the upper surface of said first support member, and
an airtight vacuum chamber defined on a side of said strain-sensing member which is opposite to said pressure-sensing portion thereof.

5. A telemetering intracranial pressure transducer according to claim 4, wherein
said first member is formed of crystalized glass having a coefficient of thermal expansion which is substantially equal to that of said strain-sensing member.

6. A telemetering intracranial pressure transducer according to claim 1, wherein
said main carrier oscillator circuit comprises
a Hartley oscillator for modulating an oscillation frequency with said subcarrier signal from said subcarrier oscillator circuit, and
a high-frequency current amplifying circuit connected to said Hartley oscillator for supplying a high-frequency electric power.

7. A telemetering intracranial pressure transducer according to claim 1, wherein
said transmitting antenna has an antenna wire being about 10 cm long and to be imbedded below the head skin of a human body, said human body serving as an antenna load.

8. A telemetering intracranial pressure transducer according to claim 1, wherein
said pressure-receiving layer is formed of silicone resin and has a modulus of elasticity of about 5 $kg/cm^2$.

9. A telemetering intracranial pressure transducer according to claim 1, wherein
said housing is made of stainless steel.

10. A telemetering intracranial pressure transducer according to claim 1, wherein
said housing comprises a cover and a casing for sealing the interior of said housing airtightly, said casing being of a cylindrical shape and having an outer peripheral surface tapered from an intermediate portion to a frontal end, and said tapered surface being provided with a screw portion for easy threaded engagement with the skull.

11. A telemetering intracranial pressure transducer comprising;
an airtight housing adapted to engage the skull of a body to be tested;
a pressure-electric transducer having a pressure-sensing portion, disposed in said housing for detecting an intracranial pressure below a dura under the skull;
a pressure-receiving layer disposed in said housing and located at a frontal end of said housing in contact with said pressure-sensing portion of said pressure-electric transducer, said pressure-receiving layer being in pressed engagement with said dura;
a transmitting circuit disposed in said housing for transmitting an output signal from said pressure-electric transducer through a transmitting antenna wherein said transmitting circuit comprises a telemetering transmission circuit connected to said pressure-electric transducer, for transmitting an output therefrom, and microbatteries for supplying electric power to said pressure-electric transducer and said telemetering transmission circuit ansd wherein said transmitting circuit further comprises switching means connected to said microbatteries for switching on and off said microbatteries; and
a receiving circuit remotely provided therefrom for receiving an output signal transmitted through said transmitting antenna of said transmitting circuit,
wherein said receiving circuit comprises
a receiving antenna for receiving a transmitted signal,
a detecting circuit connected to said receiving antenna for converting the high-frequency signal composed of the main carrier signal into an intermediate-frequency signal and demodulating the subcarrier signal through FM detection,
a subcarrier discriminator circuit connected to said detecting circuit for picking up a signal corresponding to a pressure variation from the subcarrier signal in the input signal,
a correction circuit comprising a differential amplifier having first and second input terminals and an output terminal, said first input terminal being connected to said subcarrier discriminator circuit,
a barometer connected to said second input terminal of said correction circuit, for correcting the signal therefrom, and
an indicator connected to said output terminal of said correction circuit, for indicating the corrected signal from said correction circuit.

* * * * *